United States Patent
Gall et al.

(10) Patent No.: US 10,153,062 B2
(45) Date of Patent: Dec. 11, 2018

(54) ILLUMINATION AND IMAGING DEVICE FOR HIGH-RESOLUTION X-RAY MICROSCOPY WITH HIGH PHOTON ENERGY

(71) Applicants: FRAUNHOFER-GESELLSCHAFT zur Foerderung der angewandten Forschung e.V., Munich (DE); AXO Dresden GmbH, Dresden (DE)

(72) Inventors: Martin Gall, Dresden (DE); Ehrenfried Zschech, Moritzburg (DE); Reiner Dietsch, Dresden (DE); Sven Niese, Radeburg (DE)

(73) Assignees: FRAUNHOFER-GESELLSCHAFT ZUR FOERDERUNG DER ANGEWANDTEN FORSCHUNG E.V., Munich (DE); AXO DRESDEN GMBH, Dresden (DE)

( * ) Notice: Subject to any disclaimer, the term of this patent is extended or adjusted under 35 U.S.C. 154(b) by 222 days.

(21) Appl. No.: 15/193,380

(22) Filed: Jun. 27, 2016

(65) Prior Publication Data
US 2017/0003234 A1    Jan. 5, 2017

(30) Foreign Application Priority Data
Jun. 30, 2015   (DE) ........................ 10 2015 212 230

(51) Int. Cl.
*G21K 1/06*   (2006.01)
*G21K 7/00*   (2006.01)
*G01N 23/04*  (2018.01)

(52) U.S. Cl.
CPC ............... *G21K 7/00* (2013.01); *G01N 23/04* (2013.01); *G21K 1/06* (2013.01); *G01N 2223/419* (2013.01); *G01N 2223/611* (2013.01)

(58) Field of Classification Search
CPC ...... G21K 1/06; G21K 7/00; G01N 2223/419; G01N 2223/611; G01N 23/04; G01N 23/207
See application file for complete search history.

(56) References Cited

U.S. PATENT DOCUMENTS 6,859,516 B2   2/2005   Schneider et al.
6,925,147 B2   8/2005   Lange et al.
(Continued)

FOREIGN PATENT DOCUMENTS

EP   1126477 A2   8/2001
EP   1318524 A2   6/2003

OTHER PUBLICATIONS

Niese et al., "High Precision X-Ray Multilayer Mirrors for Customized Solutions", Poster presentation at Conference "Frontiers or Characterization and Metrology for Nanoelectronics (FCMN)", (Apr. 14-16, 2015), Retrieved from the Internet: <<https://www.nist.gov/sites/default/files/documents/pml/div683/conference/33_niese.pdf>>.*

(Continued)

*Primary Examiner* — Chih-Cheng Kao
(74) *Attorney, Agent, or Firm* — Jacobson Holman, PLLC.

(57) ABSTRACT

The present invention relates to an illumination and imaging device for high-resolution X-ray microscopy with high photon energy, comprising an X-ray source (1) for emitting X-ray radiation and an area detector (4) for detecting the X-ray radiation. Moreover, the device comprises a monochromatizing and two-dimensionally focussing condenser-based optical system (2) arranged in the optical path of X-ray radiation with two reflective elements (6) being arranged side-by-side for focussing impinging X-ray radiation on an object to be imaged (5) and a diffractive X-ray lens (3) for imaging the object to be imaged (5) on the X-ray (Continued)

detector (4). Typically, the illumination and imaging device is used for performing radiography, tomography and examination of a micro-electronic component or an iron-based material.

12 Claims, 5 Drawing Sheets

(56) References Cited

U.S. PATENT DOCUMENTS

2001/0046276 A1    11/2001  Schneider et al.
2003/0108153 A1*  6/2003  Lange .................. G21K 1/06
                                                   378/85

OTHER PUBLICATIONS

Niese et al., "Full-field X-ray microscopy with crossed partial multilayer Laue lenses", Optics Express, vol. 22, No. 17, pp. 2008-20013, Aug. 12, 2014.

* cited by examiner

ILLUMINATION AND IMAGING DEVICE FOR HIGH-RESOLUTION X-RAY MICROSCOPY WITH HIGH PHOTON ENERGY

The present invention relates to an illumination and imaging device for high-resolution X-ray microscopy with high photon energy.

Devices known from prior art for examining samples using X-ray radiation make use of X-ray lenses and photon energies between 2 keV and 9 keV. Usually, an X-ray source with a copper or chromium anode with characteristic photon energies of 8,04 keV or 5,41 keV is employed. Moreover, in the condenser-based optical system, an elliptical monocapillary which exploits total reflection is used, and Fresnel zone plates serving as X-ray lenses are employed. However, monocapillaries and Fresnel zone plates can only be poorly used with photon energies above 8 keV, since the numerical aperture is limited as well due to a declining critical angle of total reflection with higher energies. By the same token, bending efficiency of the Fresnel zone plate is equally decreased as a result of the limited aspect ratio of the zones with increasing photon energy. Moreover, quality of the X-ray microscope image is reduced due to increased signal noise caused by deceleration radiation and kβ radiation.

Hence, it is an object of the present invention to create a device with which the above-mentioned drawbacks can be overcome, and which enables efficient imaging also in the presence of higher photon energies.

This object is attained by a device according to claim 1. Advantageous embodiments and further developments are described in the dependent claims.

An illumination and imaging device for high-resolution X-ray microscopy has an X-ray source for emitting X-ray radiation and an area detector for detecting X-ray radiation. A monochromatizing and two-dimensionally focussing condenser-based optical system for focussing the emitted X-ray radiation onto an object to be imaged is disposed in the optical path of the X-ray radiation. Moreover, provision is made for a diffractive X-ray lens for imaging the object to be imaged on the X-ray detector.

Use of the monochromatizing and two-dimensionally focussing condenser-based optical system, which can preferably be designed as a condenser-based optical system in a (modified) Montel geometry, as side-by-side arrangement or as arrangement according to Montel, and which is known under said designations, makes it possible to attain a high monochromatic photon flux towards the object to be imaged. Moreover, said condenser-based optical system is characterized by a compact outer shape as well as nearly identical beam characteristics in spatial directions perpendicular to the beam direction.

Moreover, such a condenser-based optical system makes it possible to realize a larger working space between the condenser-based optical system and the object plane, thereby enabling use of larger samples as objects to be imaged and utilization of systems for sample preparation or sample handling, respectively further analysis devices close to the object to be imaged. In this regard, focussing in both dimensions perpendicular to the optical axis is supposed to be understood as the two-dimensional focussing. Here, X-ray radiation is supposed to be understood as electromagnetic radiation in a wavelength range between 30 pm and 0.25 nm and, respectively or, in the energy range between 5 keV and 40 keV.

Provision can be made for the diffractive X-ray lens to be designed as a Fresnel zone plate or a crossed multilayer Laue lens. Insofar as the Fresnel zone plate is employed, a beam stop, which is also referred to as (direct) beam attenuator, is disposed between the condenser-based optical system and the object to be imaged for masking a central beam of the impinging X-ray radiation, in order to attain the required hollow cone illumination and to thereby separate in the image plane an image of the object to be imaged from undiffracted radiation. Multilayer Laue lenses, which are also referred to as "MLL", permit fast and reliable imaging also in the presence of higher energies of the photons of X-ray radiation. Typically, the multilayer Laue lens is embodied in a crossed manner, i.e. in a two-part form consisting of two components being twisted by 90° with respect to one another, in order to separate the image of the object of the undiffracted radiation in the image plane. Since the multilayer Laue lens typically only occupies zones on one side of the optical axis, another, non-rotationally-symmetrical optical path is realized. This is a difference compared to the use of a Fresnel zone plate. Hence, a hollow cone illumination is not necessary for separating the image of the object in the image plane from the undiffracted radiation. Since the multilayer Laue lens typically only has zones on one side of the optical axis, another non-rotational symmetric beam path is realized. This is a difference compared to the use of a Fresnel zone plate. Hence, hollow cone illumination is not necessary for separating the image of the object in the image plane from the undiffracted radiation.

Typically, the X-ray source is adapted to emit X-ray radiation having energy greater than 5 keV, preferably greater than 9 keV. Use of high energy X-ray photons makes it possible to also penetrate material which would feature too large an absorption length at lower energies, i.e. material which could not be penetrated. For this purpose, the X-ray source can be adapted to emit Mo-Kα radiation, Ga-Kα radiation, Ag-Kα radiation, In-Kα radiation, Cu-Kα radiation or Cr-Kα radiation.

The condenser-based optical system can include at least one reflective element which is adapted to reflect each impinging X-ray photon of the X-ray radiation exactly one time, The monochromatizing and two-dimensionally focussing condenser-based optical system can be designed as a so-called "single-bounce" optical system, i.e. typically as an X-ray mirror on which each X-ray photon is reflected only one time.

Moreover, it can be provided that the at least one reflective element is designed with a multilayer system, preferably with a multilayer system having graded layer thicknesses in order to realize a monochromatizing effect.

The condenser-based optical system preferably has two reflective elements being arranged side-by-side for monochromatizing X-ray radiation. Said two reflective elements being embodied in a side-by-side arrangement, with their reflective surfaces can be disposed at right angles to one another in order to ensure suitable beamforming and to fully illuminate the object plane. Typically, each reflective element has a curved surface contour, i.e. is configured as a plane parabola or a plane ellipse, i.e. is parabolically or elliptically curved. Preferably, the reflective elements are arranged directly side-by-side, i.e. are in direct contact with one another.

Moreover, provision is typically made for designing the reflective elements for monochromatizing X-ray radiation with a multilayer system, preferably with a multilayer system having graded layer thicknesses, in order to attain a largely monochromatic radiation. Hence, a monochromatizing and two-dimensionally focusing condenser-based optical system is realized. Since Bragg reflection is used at a multilayer system, the attainable numerical aperture is not limited by the critical angle of total reflection. Using a multilayer system further suppresses undesired radiation, such as X-ray deceleration radiation or Kβ radiation. Since the employed diffractive X-ray lenses have a high chromatic aberration, imaging quality is thereby enhanced.

The described illumination and imaging device can be employed for radiography, i.e. for recording an individual X-ray image, for tomography, i.e. for recording several X-ray images and performing a sectional image procedure, for examining a microelectronic component, which is supposed to be understood in particular as an individual integrated circuit or a three-dimensional integrated circuit, or an iron-based material, which is supposed to refer in particular to materials with a specific percentage proportion by weight or percentage proportion by volume of iron.

A method for radiography, tomography and examination of a microelectronic component or an iron-based material is typically performed with the aid of the described device.

Exemplary embodiments of the invention will be illustrated in the drawings and will be discussed in the following with reference to FIGS. 1 to 5, wherein.

Figure 1:
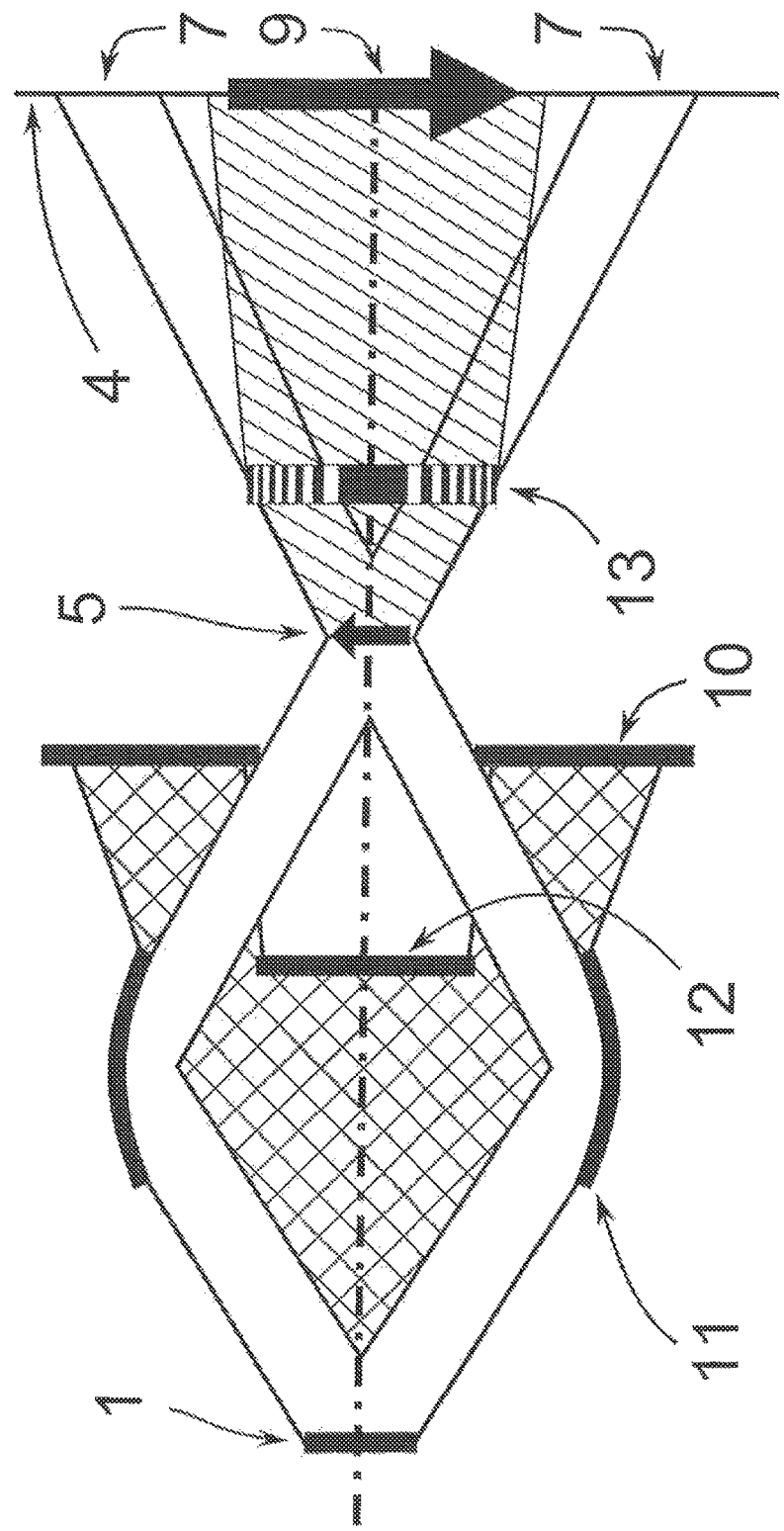
FIG. 1 is an optical path of an X-ray device according to prior art in a lateral view.

FIG. 1 shows an optical path of an X-ray device according to prior art in a lateral view. Here, the optical path is rotationally symmetrical with a capillary condenser 11 (as a section from a spheroid) and a Fresnel zone plate 13. Starting from an X-ray source 1, emitted X-ray radiation is deflected via the capillary condenser in the form of hollow cone illumination onto the object to be imaged. Undesired and interfering portions of the radiation of the X-ray radiation emitted by the X-ray source 1 are blocked by means of a beam stop 12 and an aperture 10, so that they do not impinge on the detector 4. By means of the Fresnel zone plate 13 X-ray radiation reaches the X-ray detector 4. An image 9 of the object to be imaged 5 is produced on the detector 4. Moreover, beams 7 which have not been diffracted by the Fresnel zone plate 13 are discernible on the detector 4.

Figure 2:
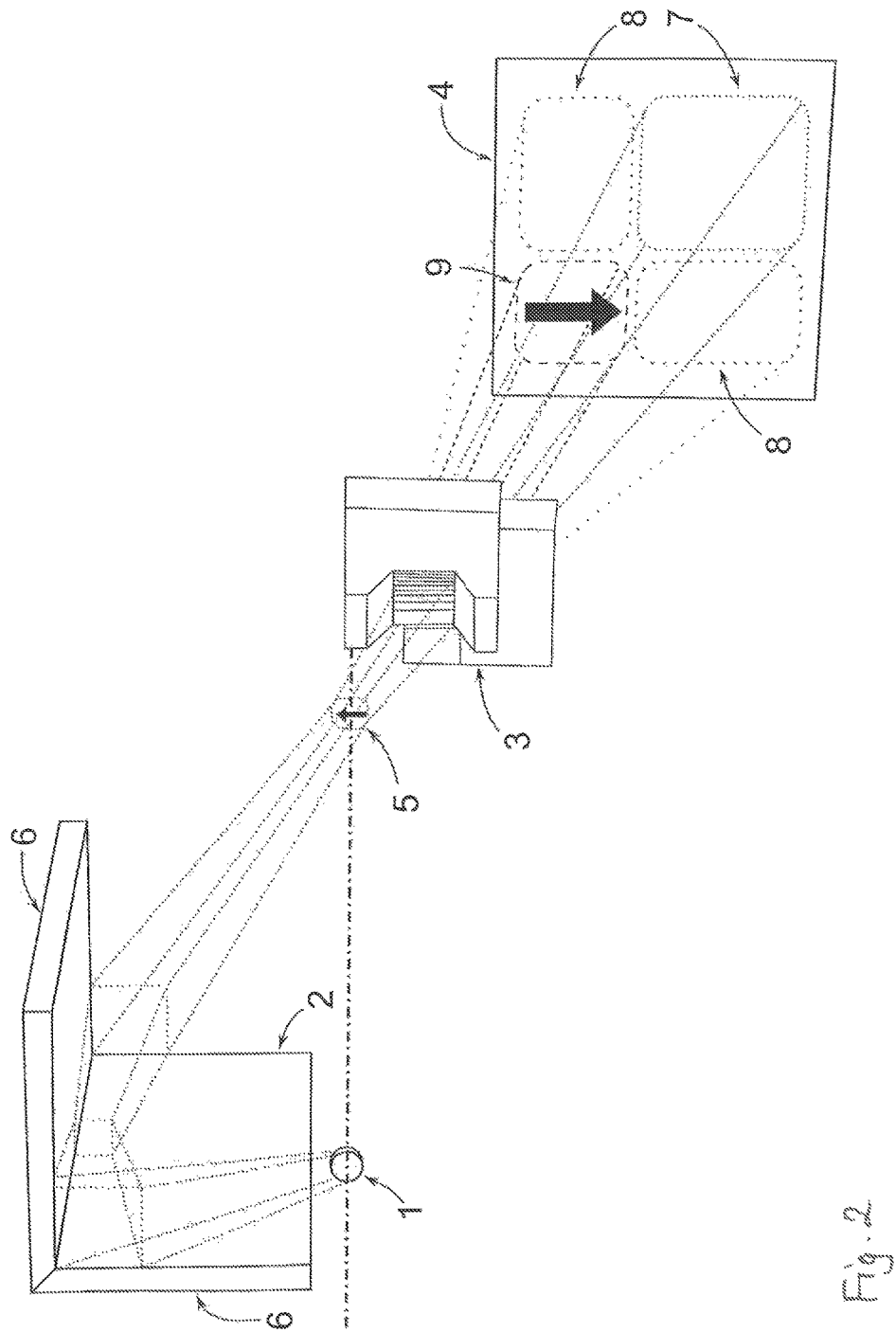
FIG. 2 is a schematic representation of a device with a multilayer Laue lens.

FIG. 2, by contrast, in a schematic representation shows a device which can be employed for performing radiography or tomography, respectively for examining a microelectronic component or an iron-based material, and which enables full illumination instead of hollow cone illumination. Recurring features in this Figure as well as in the following Figures are furnished with identical reference numerals.

The X-ray source 1 emits X-ray radiation in a cone-beam shape, which impinges onto a condenser-based optical device 2. The condenser-based optical device 2 is configured as a side-by-side arrangement and is composed of two reflective elements 6 which are arranged directly side-by-side. Said two reflective elements 6 are disposed at right angles to one another and are designed with a multilayer system having graded layer thicknesses. The thickness gradient of the individual layers is derived from the respectively locally different angles of incidence and the respective wavelength of the X-ray radiation. In the exemplary embodiment as represented in FIG. 1, the reflective elements 6 are curved elliptically, and, in other embodiments can also be curved parabolically, or use can made of a combination of parabolic curvature and elliptical curvature at respectively one of the reflective elements 6. In order to attain a two-dimensional beamforming of the condenser-based optical device 2, reflection is required at both reflective elements 6 in the form of elementary mirrors.

The X-ray radiation reaches the object to be imaged 5, which is arranged between the condenser-based optical system 2 and a multilayer Laue lens as diffractive X-ray lens 3, from the monochromatizing and two-dimensionally focusing condenser-based optical device 2. Said multilayer Laue lens in turn images the object to be imaged 5 on the X-ray detector 4. Said X-ray detector 4 is a spatial resolving area detector with a pixel size of typically 0.5 μm to 6 μm. Only the beams 8 which have been diffracted by only one of the two crossed components of the multilayer Laue lens are equally discernible on the detector 4.

The X-ray source 1 in the represented exemplary embodiment is an X-ray source with a rotating molybdenum anode, and thus makes use of Mo-Kα radiation having a photon energy of 17,45 keV. In further exemplary embodiments, the X-ray source 1 can also have a rotating silver anode or may be an X-ray source composed of liquid gallium or indium. Accordingly, Ga-Kα radiation having energy of 9,24 keV or In-Kα radiation having energy of 24,1 keV can be used. Typically, X-ray photons having energy greater than 5 keV, preferably, however, X-ray photons having energy greater than 9 keV are used.

The multilayer Laue lens is configured in a crossed manner. In this two-part configuration, the two components of the multilayer Laue lens are straightly twisted by 90° with respect to one another and are consecutively arranged along the optical axis which is plotted using a dashed line. in this way, correct imaging of the object to be examined 5 is realized in both directions perpendicular to the optical axis, in contrast to a Fresnel zone plate, high diffraction efficiency is maintained, since the multilayer Laue lens has been excised from a multilayer stack and thus provides for an optimum aspect ratio of the zones for corresponding photon energies. In the represented exemplary embodiment, the multilayer Laue lens has 2450 zones with a width between 10 nm and 80 nm in accordance with zone plate law.

Figure 3:
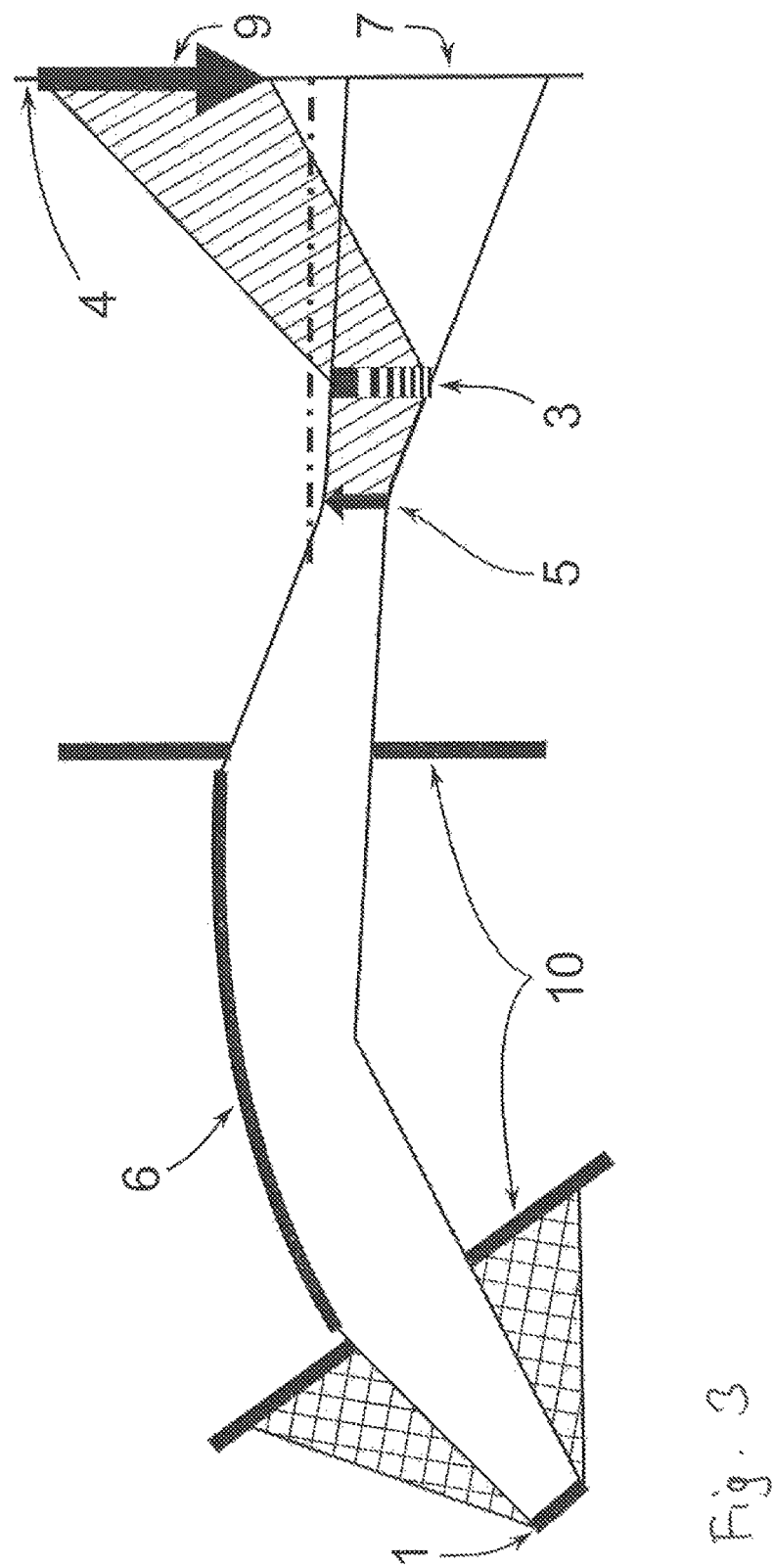
FIG. 3 is a lateral view according to FIG. 1 of an optical path in the device shown in FIG. 2.

FIG. 3 in a lateral view corresponding to FIG. 1 shows a portion of the optical path of the device as shown in FIG. 2 Here, for simplification, only a one-dimensional image of the object to be imaged 5 is shown with a single multilayer Laue lens and merely one reflective element 6. Direct X-ray radiation of the X-ray source 1, which is not reflected at the condenser-based optical system 6, is suppressed with the aid of apertures 10 and does not reach the detector 4 in the form of interfering noise. The image 9, however, has to be separated in the image plane from the undiffracted beams 7 and the beams 8 diffracted only at one of the two components of the multilayer Laue lens.

Figure 4:
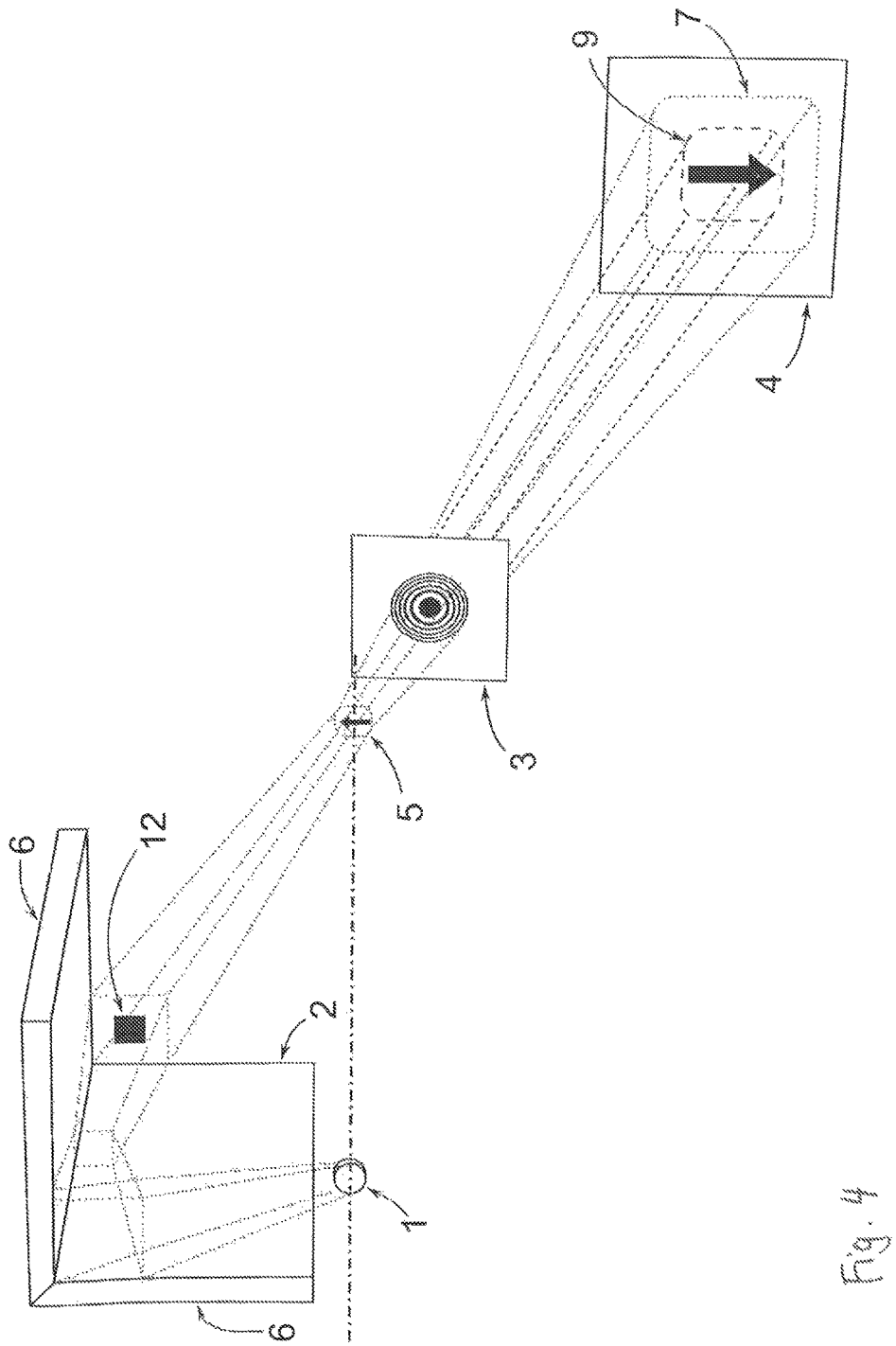
FIG. 4 is a representation of a device with a Fresnel zone plate in accordance with FIG. 2.

FIG. 4, in a view corresponding to FIG. 2, shows another embodiment of the device, in which a Fresnel zone plate, however, is employed as diffractive X-ray lens 3 instead of a multilayer Laue lens. Moreover, for masking a central beam a beam stop 12 is disposed between the condenser-based optical system 2 and the object to be imaged 5. In contrast to the beam stop 12 as shown in FIG. 1, the beam stop 12 as shown in FIG. 4, however, does not serve the purpose of suppressing radiation directly emanating from the X-ray source 1, but the beam stop 12 is rather required for realizing the hollow cone illumination.

In both cases, i.e. use of the multilayer Laue lens as represented in FIGS. 2 and 3, and use of the Fresnel zone plate as represented in FIG. 4, in contrast to prior art as reproduced in FIG. 1, an aperture 10 close to the object to be imaged is not necessary, so that working distance is increased.

Figure 5:
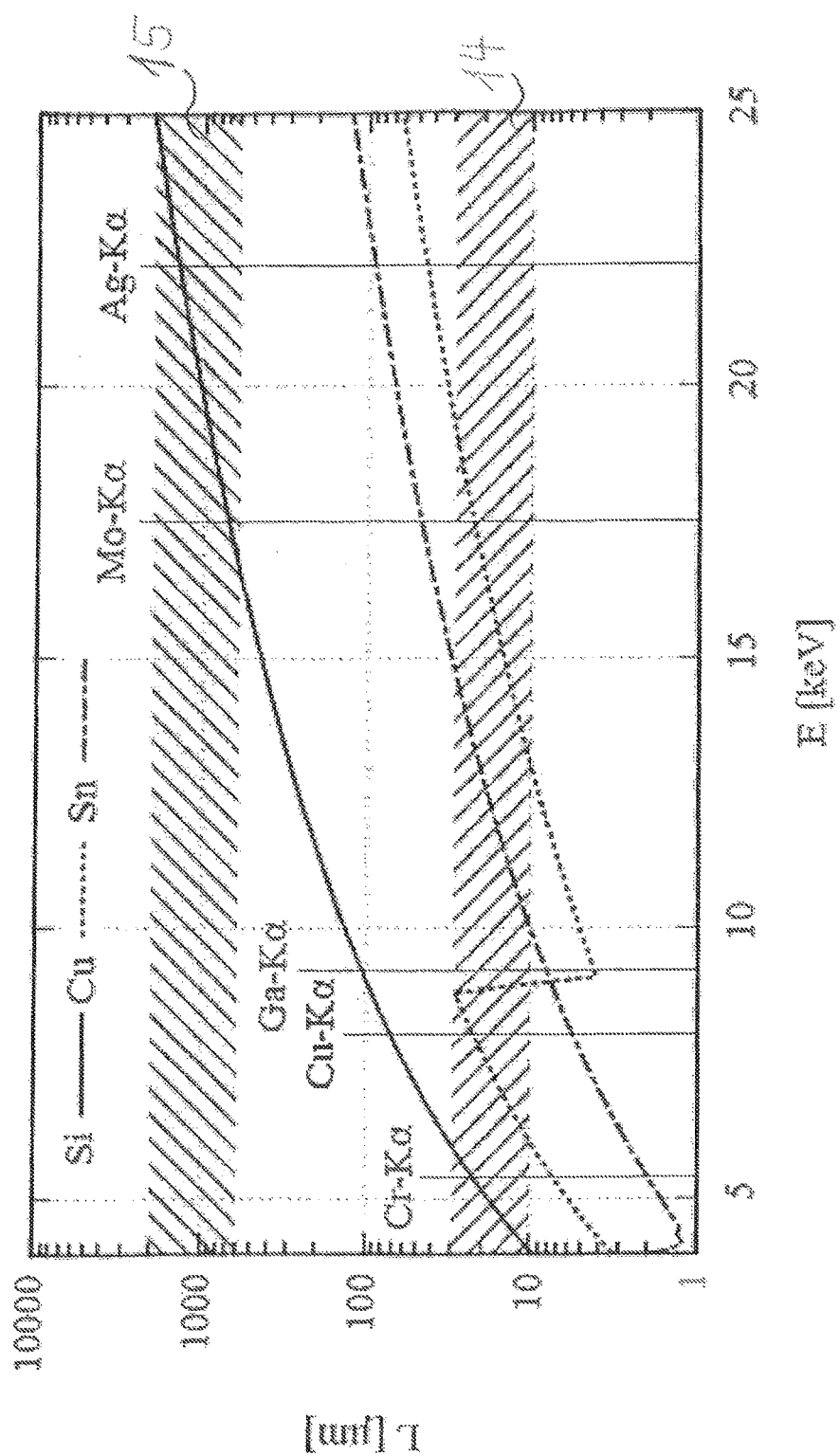
FIG. 5 is a diagram showing absorption lengths of different materials.

FIG. 5 finally shows a diagram, in which photon energy E is plotted in keV on an x-axis and an absorption length L given in um is plotted on a y-axis. Moreover, the curves represent the absorption curves for three materials frequently used for microelectronic components, namely silicon, copper and tin. The plotted vertical lines represent the characteristic photon energies of selected anode materials. The absorption lengths of the anode materials result from the respective intersection of the represented characteristic photon energy with the absorption curves. Finally, a horizontal band 14 represents a typical thickness of copper components in microelectronic components which can consequently be penetrated by the represented characteristic photon energies. A horizontal band 15 represents a thickness of typical silicon substrates in microelectronic components which are equally to be penetrated. It can be seen from this figure that in particular use of Mo-Kα radiation enables both, penetration of the silicon substrate and good imaging of copper structures, since the thickness to be respectively penetrated corresponds to the absorption length.

The described device thus provides a new approach for X-ray imaging both in microscopy and tomography using an X-ray source emitting X-ray radiation having a high photon energy of greater than 5 keV, preferably greater than 9 keV, the condenser-based optical system 2 with a multilayer structure which monochromatizes X-ray radiation emanating from the X-ray source 1 and images the same on a focal point, whereby the numerical aperture is adapted to the subsequently arranged X-ray lens 3, Said diffractive X-ray lens 3 finally images the object to be imaged 5 on an image plane, in which the X-ray detector 4 is located.

This device preferably can be used in the examination of microelectronic components, since the higher photon energies increase the penetrative capability of silicon substrates compared to known solutions At the same time, as is also shown in FIG. 4, the absorption length for materials of interest in this regard lies in a favourable range in order to achieve a good imaging contrast. Thus, highly resolved X-ray images with reduced or even omitted sample preparation can be achieved. Particularly preferably, the device and a method in which said device is used are employed in the examination of microelectronic components, such as individual chips or three-dimensional integrated chips.

Merely features disclosed in the exemplary embodiments of the different embodiments can be combined and claimed individually.

The invention claimed is:

1. Illumination and imaging device for high-resolution X-ray microscopy with high photon energy, comprising:
   an X-ray source (1) for emitting X-ray radiation,
   an area detector (4) for detecting X-ray radiation,
   a monochromatizing and two-dimensionally focusing condenser-based optical system (2) which is arranged in the optical path of the X-ray radiation for focusing impinging X-radiation onto an object to be imaged (5), said condenser-based optical system (2) having two reflective elements (6) being arranged side-by-side and disposed at right angles to one another for monochromatizing X-ray radiation, each of said reflective elements (6) having a parabolically or elliptically curved shaped, and
   a diffractive X-ray lens (3) for imaging the object to be imaged (5) on the X-ray detector (4).

2. Illumination and imaging device according to claim 1, characterized in that the diffractive X-ray lens (3) is a Fresnel zone plate disposed between the condenser-based optical system (2) and the object to be imaged (5) with a beam stop (9) for masking a central beam of the impinging X-ray radiation.

3. Illumination and imaging device according to claim 1, characterized in that the X-ray source (1) is adapted to emit X-ray radiation having energy greater than 5 keV.

4. Illumination and imaging device according to claim 3, characterized in that the X-ray source (1) is adapted to emit Mo-Kα radiation, Ag-Kα radiation, Ga-Kα radiation, In-Kα radiation, Cu-Kα radiation or Cr-Kα radiation.

5. Illumination and imaging device according to claim 1, characterized in that the condenser-based optical system (2) includes at least one reflective element (6) which is adapted to reflect each impinging X-ray photon of the X-ray radiation exactly one time.

6. Illumination and imaging device according to claim 5, characterized in that the at least one reflective element (6) is designed with a multi-layer system.

7. Illumination and imaging device according to claim 5, characterized in that the at least one reflective element (6) is designed with a multilayer system having graded layer thicknesses.

8. Illumination and imaging device according to claim 1, characterized in that the two reflective elements (6) are arranged directly side-by-side.

9. Illumination and imaging device according to claim 1, characterized in that the reflective elements (6) for monochromatizing X-ray radiation are designed with a multilayer system.

10. Illumination and imaging device according to claim 1, characterized in that the diffractive X-ray lens (3) is a crossed multilayer Laue lens.

11. Illumination and imaging device according to claim 1, characterized in that the X-ray source (1) is adapted to emit X-ray radiation having energy greater than 9 keV.

12. Illumination and imaging device according to claim 1, Characterized in that the reflective elements (6) for monochromatizing X-ray radiation with a multilayer system having graded layer thicknesses.

* * * * *